United States Patent
Murase

(10) Patent No.: US 9,746,537 B2
(45) Date of Patent: Aug. 29, 2017

(54) MAGNETIC RESONANCE IMAGING APPARATUS AND MAGNETIC RESONANCE IMAGING METHOD

(71) Applicant: HITACHI, LTD., Tokyo (JP)

(72) Inventor: Takenori Murase, Tokyo (JP)

(73) Assignee: HITACHI, LTD., Tokyo (JP)

( * ) Notice: Subject to any disclaimer, the term of this patent is extended or adjusted under 35 U.S.C. 154(b) by 433 days.

(21) Appl. No.: 14/398,745

(22) PCT Filed: Aug. 28, 2013

(86) PCT No.: PCT/JP2013/072966
§ 371 (c)(1),
(2) Date: Nov. 4, 2014

(87) PCT Pub. No.: WO2014/038441
PCT Pub. Date: Mar. 13, 2014

(65) Prior Publication Data
US 2015/0276905 A1    Oct. 1, 2015

(30) Foreign Application Priority Data

Sep. 6, 2012 (JP) ................................ 2012-196068

(51) Int. Cl.
*G01R 33/56* (2006.01)
*G01R 33/565* (2006.01)
(Continued)

(52) U.S. Cl.
CPC .......... *G01R 33/565* (2013.01); *A61B 5/0037* (2013.01); *A61B 5/055* (2013.01);
(Continued)

(58) Field of Classification Search
CPC .. G01R 33/565; G01R 33/385; G01R 33/387; G01R 33/543; G01R 33/56563;
(Continued)

(56) References Cited

U.S. PATENT DOCUMENTS 5,162,737 A * 11/1992 Nozokido .......... G01R 33/4828
                                                              324/307
5,371,465 A * 12/1994 Onodera ............ G01R 33/3875
                                                              324/307
(Continued)

FOREIGN PATENT DOCUMENTS

JP      2001-238866        9/2001

OTHER PUBLICATIONS

International Search Report in PCT/JP2013/072966.
Wu, Pei-Hsin et al., "Accurate B0 mapping with an adaptive algorithm integrating KESA, PRELUDE, and time-domain phase unwrapping", Proc. Intl. Soc. Mag. Reson. Med., vol. 20, 2012, p. 2506.

*Primary Examiner* — Clayton E LaBalle
*Assistant Examiner* — Ruifeng Pu
(74) *Attorney, Agent, or Firm* — Cooper & Dunham LLP

(57) ABSTRACT

In order to eliminate a global phase change caused by static magnetic field inhomogeneity included in a nuclear magnetic resonance signal, focusing on that phase components generated in a nuclear magnetic resonance signal caused by the static magnetic field inhomogeneity is in a predetermined frequency band (low-frequency band), phase components in the frequency band caused by the static magnetic field inhomogeneity is eliminated from an image generated from the nuclear magnetic resonance signal in main imaging. The predetermined frequency band of the phase components caused by the static magnetic field inhomogeneity is calculated from the nuclear magnetic resonance signal obtained in preliminary imaging.

12 Claims, 14 Drawing Sheets

(51) Int. Cl.
  *A61B 5/055* (2006.01)
  *A61B 5/00* (2006.01)
  *G01R 33/385* (2006.01)
  *G01R 33/387* (2006.01)
  *G01R 33/54* (2006.01)
  *G06T 11/00* (2006.01)

(52) U.S. Cl.
  CPC .......... *A61B 5/7203* (2013.01); *G01R 33/385* (2013.01); *G01R 33/387* (2013.01); *G01R 33/543* (2013.01); *G01R 33/56563* (2013.01); *G06T 11/005* (2013.01); *G01R 33/5608* (2013.01)

(58) Field of Classification Search
  CPC ... G01R 33/5608; G06T 11/005; A61B 5/055; A61B 5/7203
  See application file for complete search history.

(56) References Cited

U.S. PATENT DOCUMENTS

| | | | |
|---|---|---|---|
| 5,942,897 A * | 8/1999 | Kanazawa | G01R 33/56518 324/307 |
| 6,515,476 B1 * | 2/2003 | Oshio | G01R 33/243 324/307 |
| 2009/0256567 A1 | 10/2009 | Aksit et al. | |
| 2010/0177944 A1 * | 7/2010 | Madabhushi | G06K 9/6231 382/131 |
| 2015/0276904 A1 * | 10/2015 | Grodzki | A61B 5/055 324/309 |
| 2015/0285887 A1 * | 10/2015 | Bollenbeck | G01R 33/3621 324/322 |

* cited by examiner

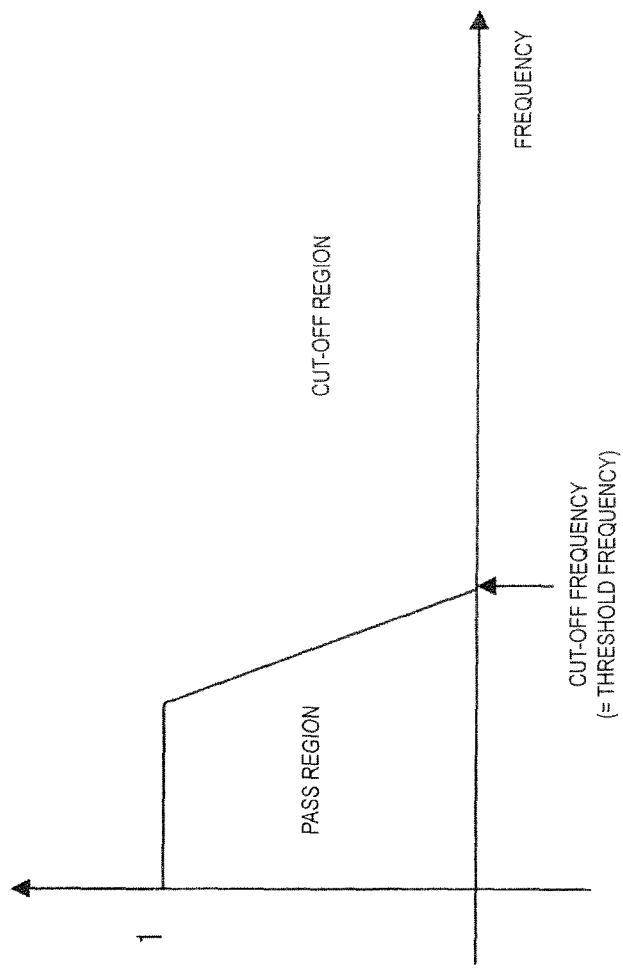

MAGNETIC RESONANCE IMAGING APPARATUS AND MAGNETIC RESONANCE IMAGING METHOD

TECHNICAL FIELD

The present invention relates to a magnetic resonance imaging (hereinafter, referred to as MRI) apparatus, and in particular to an MRI apparatus including a unit to correct artifacts caused by static magnetic field inhomogeneity.

BACKGROUND ART

An MRI apparatus is a medical image diagnostic apparatus that applies a high-frequency magnetic field and a gradient magnetic field to an object placed in a static magnetic field and measures a signal generated from the object by nuclear magnetic resonance to visualize to image the object. In an MRI apparatus, a slice gradient magnetic field that generally identifies an imaging surface is applied at the same time when an excitation pulse (high-frequency magnetic field pulse) that excites magnetization in the surface is provided to obtain a nuclear magnetic resonance signal (echo) to be generated in a stage where the excited magnetization converges. At this point, in order to provide positional information to the magnetization, a phase encoding gradient magnetic field in a mutually vertical direction in the imaging surface and a read-out gradient magnetic field are applied while the echo is obtained after the excitation. The measured echo is placed in a k-space whose horizontal axis is kx and the vertical axis is ky to reconstruct an image by performing inverse Fourier transform for the echo in the k-space.

A pixel value of a reconstruction image is a complex value including absolute value information and phase information. The absolute value and the phase are determined by an imaging sequence type, an imaging parameter comprised of a pixel size, a repetition time, etc., a magnetization density in an object and the relaxation time, spatial distribution of a resonance frequency, etc. As a normal reconstruction image, although there are many cases where a gray-scale image whose absolute value is a pixel value is used, a method to generate an image by combining an absolute value with a phase.

For example, the patent literature 1 discloses that a phase of each pixel of a reconstruction image is converted into a value whose value range is [−π,π] to generate a phase image, additionally, a phase mask where a value range of the phase image was converted into [0, 1] is created, and a product of a value which is a q-th power (q≥1) of each pixel phase of the phase mask and an absolute value of the same pixel is calculated to generate an image whose pixel value is the calculated product. The value q is determined so that the contrast-noise ratio becomes the maximum. A high contrast image can be obtained by this process.

On the other hand, the patent literature 2 discloses that static magnetic field intensity distribution is calculated from two phase distribution images whose echo time was shifted by Δt using that static magnetic field intensity information is reflected to a phase value of the echo. The static magnetic field intensity distribution is used to perform shimming.

Also, the non-patent literature 1 discloses that phase correction is performed for an echo signal in a k-space using the echo signal obtained in zero-encoding. A process to delete phase information caused by static magnetic field inhomogeneity by performing a high-pass filter process or low-pass filter process for an echo in the k-space is also known.

CITATION LIST

Patent Literature

PTL 1: Description of U.S. Pat. No. 6,658,280
PTL 2: Japanese Unexamined Patent Application Publication No. 2001-238866

Non-patent Literature

NPL 1: Edited by E. MARK HAACKE and JURGEN R. REICHENBACH, "SUSCEPTIBILITY WEIGHTED IMAGING IN MRI Basic Concepts and Clinical Applications", WILEY-BLACKWELL, p. 622-626

SUMMARY OF INVENTION

Technical Problem

If inhomogeneity is found in a static magnetic field generated by a static magnetic field generation device of an MRI apparatus, a rotation that is more than or equal to a phase rotation to be originally induced by object magnetization occurs, and the inhomogeneity appears as artifacts in an image. Therefore, it is difficult to completely correct an inhomogeneous static magnetic field with the method to correct the inhomogeneous static magnetic field using a shim coil etc. as described in PTL 2.

Also, the method to perform phase correction for an echo in a k-space using a zero-encoding echo disclosed in NPL 1 cannot correct only phase information caused by static magnetic field inhomogeneity.

Although a process to delete phase information caused by static magnetic field inhomogeneity by performing a high-pass filter process or low-pass filter process for an echo in a k-space is also known, there are a case where artifacts remains in an image and a case where important phase information other than phase information caused by the static magnetic field inhomogeneity is deleted.

The present invention was made in light of the above problems and has a purpose to provide a technique to eliminate a global phase change caused by static magnetic field inhomogeneity included in a nuclear magnetic resonance signal.

Solution to Problem

The present invention focuses on that phase components generated in a nuclear magnetic resonance signal caused by static magnetic field inhomogeneity is in a predetermined frequency band and eliminates the phase components in the frequency band caused by the static magnetic field inhomogeneity from an image generated from the nuclear magnetic resonance signal in main imaging. The predetermined frequency band of the phase components caused by the static magnetic field inhomogeneity is calculated from the nuclear magnetic resonance signal obtained in preliminary imaging.

Advantageous Effects of Invention

According to the present invention, since a frequency range of phase components caused by static magnetic field inhomogeneity can be calculated from a nuclear magnetic resonance signal obtained in preliminary imaging, the phase components caused by the static magnetic field inhomogeneity can be eliminated by signal processing for a nuclear magnetic resonance signal obtained in main imaging. Therefore, regardless of factors such as a static magnetic field intensity, an imaging sequence, an imaging parameter, a magnetization density in an object, and a relaxation time and an imaging method of main imaging, artifacts due to the inhomogeneous static magnetic field can be reduced.

BRIEF DESCRIPTION OF DRAWINGS

FIG. 14 is a graph showing a low-frequency region pass filter of the fourth embodiment.

DESCRIPTION OF EMBODIMENTS

The present invention focuses on that a signal component (phase component) by a phase rotation of magnetization caused by static magnetic field inhomogeneity included in a nuclear magnetic resonance signal is shown as a predetermined frequency band (specifically, low-frequency band), the phase components caused by the static magnetic field inhomogeneity is eliminated from at least either of a nuclear magnetic resonance signal obtained in main imaging or an image reconstructed from the nuclear magnetic resonance signal in main imaging. Phase information generated by static magnetic field inhomogeneity from a nuclear magnetic resonance signal obtained by preliminary imaging is obtained to calculate a range of a predetermined frequency band (low-frequency band) caused by the static magnetic field inhomogeneity. Hence, in an image to be obtained in desired main imaging, artifact reduction by phase components caused by the static magnetic field inhomogeneity is achieved. Hereinafter, the embodiments of the present invention will be described specifically.

Figure 1:
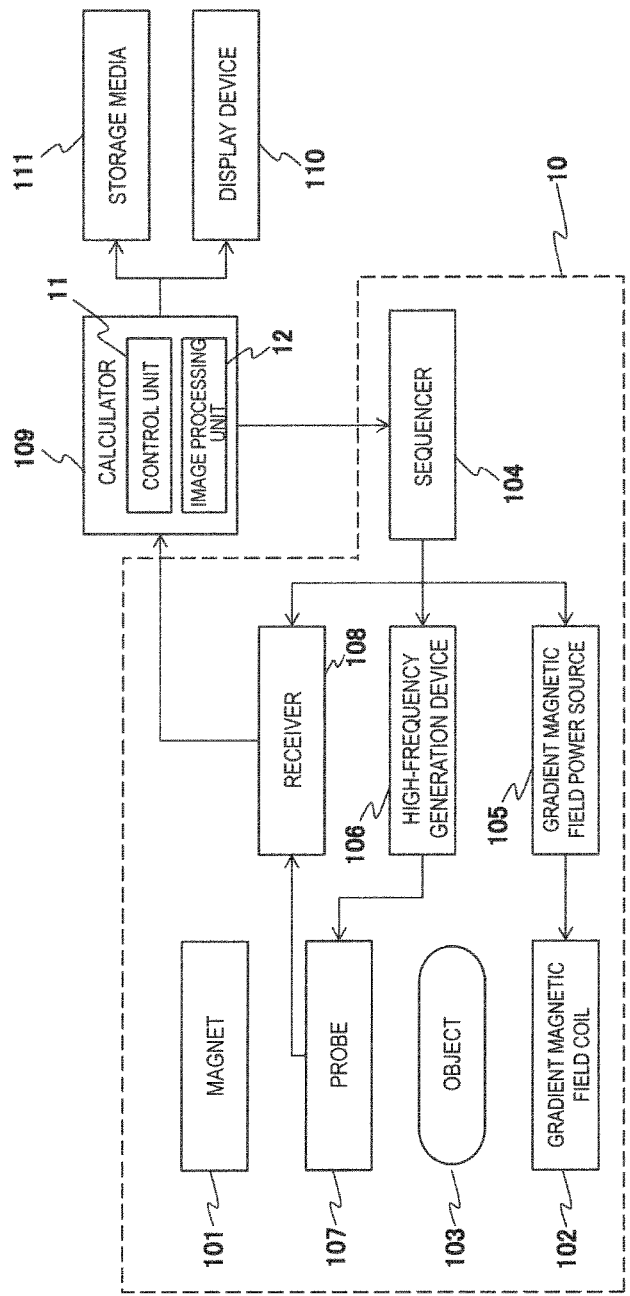
FIG. 1 is a block diagram showing an overall configuration of an MRI apparatus of the embodiments of the present invention.
Figure 2:
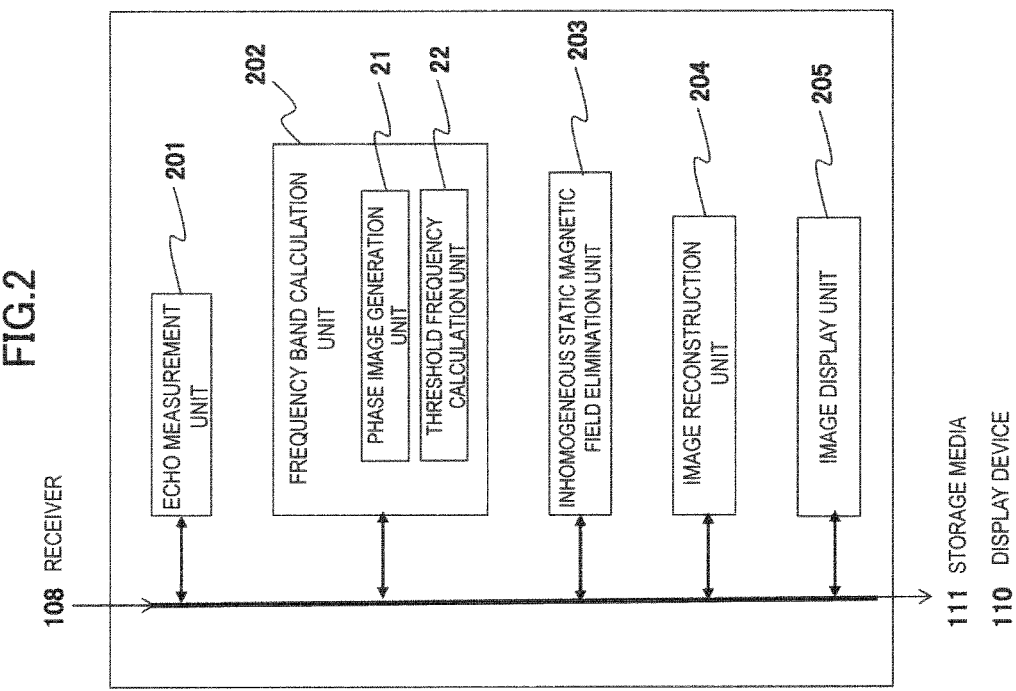
FIG. 2 is a block diagram showing a detailed configuration of an image processing unit.

The configuration of an MRI apparatus of the present embodiment is described using FIGS. 1 and 2. As shown in FIG. 1, the MRI apparatus applies a high-frequency magnetic field and a gradient magnetic field to the object 103 placed in a static magnetic field and is comprised of the imaging unit 10 detecting a nuclear magnetic resonance signal to be generated from the object 103, the control unit 11 controlling operations of the imaging unit 10, and the image processing unit 12 performing calculation for the nuclear magnetic resonance signal and generating an image. The control unit 11 allows the imaging unit 10 to execute predetermined preliminary imaging and main imaging. As shown in FIG. 2, the image processing unit 12 includes the frequency band calculation unit 202 calculating a frequency band of phase components caused by static magnetic field inhomogeneity from a nuclear magnetic resonance signal obtained by preliminary imaging and the inhomogeneous static magnetic field elimination unit 203 to eliminate phase components of a low-frequency band from an image generated from a nuclear magnetic resonance signal obtained by main imaging. Hereinafter, further description is continued.

Figure 10:
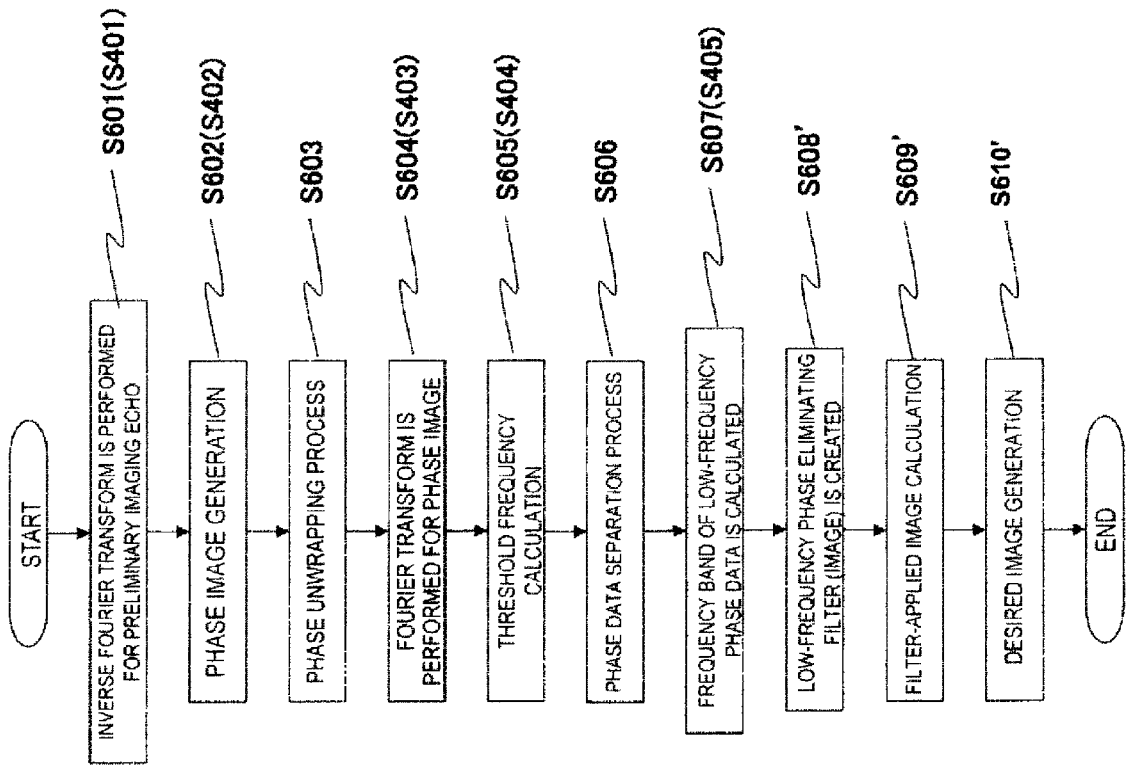
FIG. 10 is a flow chart showing a processing procedure of the second embodiment.

The imaging unit 10, as shown in FIG. 10, is comprised of the magnet 101 generating a homogeneous static magnetic field in an imaging space where the object 103 is to be placed, the gradient magnetic field coil 102 generating a gradient magnetic field in the imaging space, the probe 107 irradiating a high-frequency magnetic field in the imaging space as well as detecting a nuclear magnetic resonance signal (hereinafter, referred to as an echo), the gradient magnetic field power source 105 supplying current to the gradient magnetic field coil 102, the high-frequency generation device 106 supplying high-frequency voltage to the probe 107, the receiver 108 detecting an echo that the probe 107 detected, and the sequencer 104. The object (for example, a living body) 103 is to be placed on a bed (table) etc. and is to be positioned in an imaging space.

The control unit 11 controls operations of the sequencer 104, and it executes imaging with a predetermined imaging method and in imaging conditions. Specifically, the sequencer 104 sends commands respectively to the gradient magnetic field power source 105 and the high-frequency generation device 106 at a timing when a predetermined imaging method is achieved, generates a current/voltage signal, and supplies them respectively to the gradient magnetic field coil 102 and the probe 107. The gradient magnetic field coil 102 and the probe 107 generate a gradient magnetic field and a high-frequency magnetic field respectively and apply them to the object 103. An echo generated from the object 103 is received by the probe 107 and detected by the receiver 108. A nuclear magnetic resonance frequency (detection reference frequency f0) that is a reference of the detection by the receiver 108 is set by the sequencer 104. The detected signal is to be sent to the calculator 109.

The sequencer controls so that each unit operates at a timing and intensity programmed in advance. Particularly, a program where a high-frequency magnetic field, a gradient magnetic field, and a timing and intensity of signal reception are described is referred to as a pulse sequence. Various pulse sequences according to imaging purposes are known. The control unit 11 provides a command to select a pulse sequence type to and performs the above timing and intensity settings for the sequencer 104. This controls imaging so as to be executed with a predetermined imaging method.

The control unit 11 and the image processing unit 12 are disposed in the calculator 109. The CPU in the calculator 109 reads and executes a program stored in a built-in memory that is not shown in the diagram to achieve the respective functions of the control unit 11 and the image processing unit 1.

Also, inside the image processing unit 12, as shown in FIG. 2, the frequency band calculation unit 202, the inhomogeneous static magnetic field elimination unit 203, the echo measurement unit 201 arranging echoes detected by the receiver 108 in a k-space, the image reconstruction unit 204 reconstructing an image from data arranged in the k-space, and the image display unit 205 displaying the obtained image on the display device 110 are included. In order to achieve these respective units, the CPU in the calculator 109 also reads and executes a pre-stored program.

The calculator 109 is connected to the display device 110 and the storage media 111 to display an image etc. obtained by image processing. Detected signals and measurement conditions may be memorized in the storage media 111 as needed.

Next, a flow of the imaging process of the present embodiment will be described using the flow chart in FIG. 3.

The control unit 11 allows the imaging unit 10 to execute a predetermined preliminary imaging sequence (S301). In the preliminary imaging sequence, two sets of nuclear magnetic resonance signals (echoes) with the echo time (TE) shifted by a predetermined time ($\Delta t$) are obtained to image a predetermined site. For example, while a phase encoding amount is being changed by setting an echo time to T0, a preliminary imaging sequence of measuring to obtain a predetermined number of echoes required for image generation and measuring to similarly obtain a predetermined number of echoes by setting the echo time to T0+$\Delta t$ ($\Delta t \neq 0$) is performed. It is desired that imaging conditions of the two measurements are the same other than the echo time. Also, it is desired that preliminary imaging is performed in a state where the object 103 is disposed in an imaging space.

A preliminary imaging sequence is performed similarly to a normal imaging sequence (such as a spin echo sequence and a gradient echo sequence) other than shifting an echo time by $\Delta t$. Also, a known imaging sequence to calculate static magnetic field intensity distribution (for example, the sequence disclosed in PTL 2 (FIG. 1)) can be used.

In the two measurements of the preliminary sequence, the receiver 108 detects and obtains two sets of echoes, the echo measurement unit 201 of the image processing unit 12 arranges the echoes in a k-space, and additionally, a difference of signal values are calculated between the same positions in the k-space. Because phase information proportional to time when inhomogeneity of a static magnetic field intensity is perceived and phase information by the other conditions are provided to the two sets of echoes, calculation for a difference of both the echoes can obtain an echo where phase information by an element other than static magnetic field inhomogeneity was reduced. An echo obtained by the difference is hereinafter referred to as the preliminary imaging echo 501.

The preliminary imaging echo is a complex number.

Figure 3:
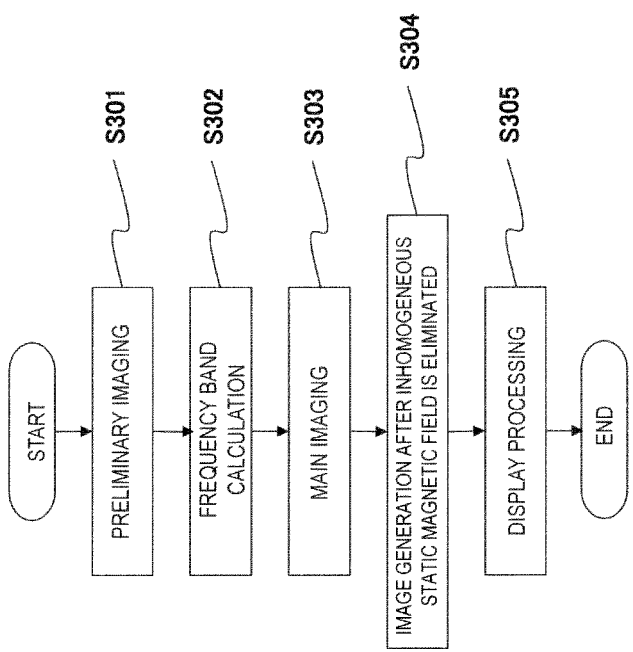
FIG. 3 is a flow chart showing operations of imaging and image generation of the embodiments of the present invention.
Figure 4:
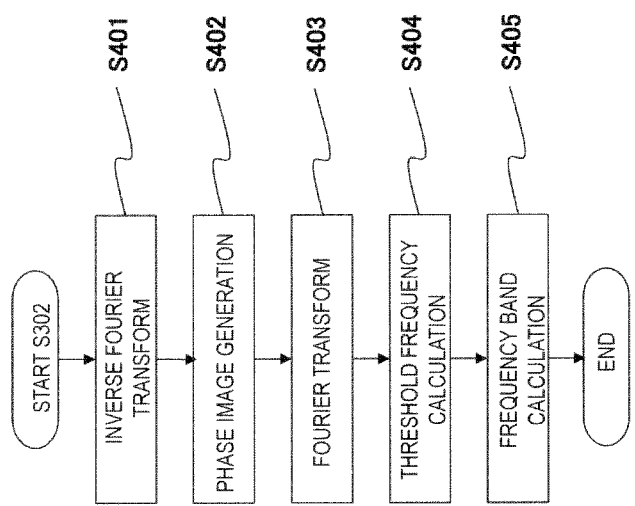
FIG. 4 is a flow chart showing a detailed operation of Step S302 in FIG. 3.
Figure 5:
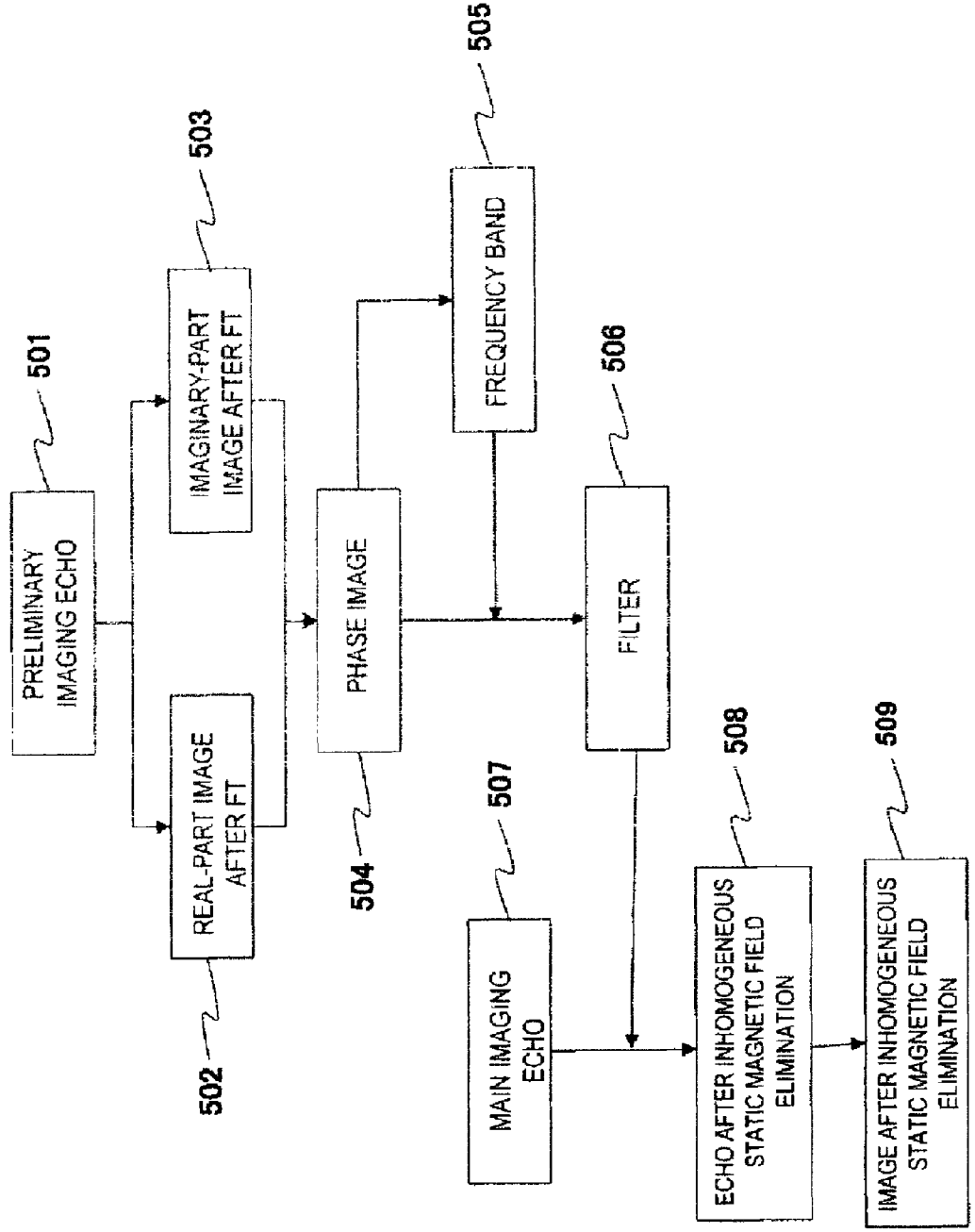
FIG. 5 is an explanatory diagram showing an image and signal to be obtained in the flow process of FIG. 3.

The frequency band calculation unit 202 of the image processing unit 12 calculates a frequency band of phase components caused by static magnetic field inhomogeneity from the preliminary imaging echo 501 (S302 in FIG. 3). The S302 process is described in detail using diagrams showing the flow of FIG. 4 and the data flow of FIG. 5. The phase image generation unit 21 in the frequency band calculation unit 202 performs inverse Fourier transform (FT) for the preliminary imaging echo 501 disposed in a k-space (S401 in FIG. 4). Hence, as shown in FIG. 5, the real-part image 502 and the imaginary-part image 503 are obtained from the preliminary imaging echo 501. The phase image generation unit 21 calculates a phase value of each pixel from the real-part image 502 and the imaginary-part image 503 to generate the phase image 504 (S402). The phase image shows distribution of phase differences of the two sets of echoes obtained in preliminary imaging in a real space and reflects inhomogeneity of a static magnetic field intensity.

The frequency band calculation unit 202 of the threshold frequency calculation unit 22 calculates the frequency band 505 of phase components caused by static magnetic field inhomogeneity from the phase image 504 (FIG. 5). First, the threshold frequency calculation unit 22 performs Fourier transform for the phase image 504 to obtain data (phase data) after the Fourier transform (S403 in FIG. 4). Utilizing that the phase components caused by static magnetic field inhomogeneity appears in a low-frequency, a frequency band of phase data caused by the static magnetic field inhomogeneity is calculated from frequency distribution of the phase data. Specifically, based on the frequency distribution of the phase data, a threshold frequency to separate into high-frequency data and low-frequency data is calculated. A frequency band equal to or less than the threshold frequency of the phase data is specified as a frequency band of the phase components caused by the static magnetic field inhomogeneity (S404 and S405). As a process to calculate a threshold frequency based on frequency distribution, various methods can be used. As an example, at least one process of a discriminant analysis method, weighted average method, addition-averaging method, p-tile method, etc. is performed for a frequency distribution histogram of phase data to calculate the center of the histogram, and the center can be specified as a threshold frequency.

Next, the control unit 11 allows the imaging unit 10 to execute a desired main imaging sequence set by an operator to obtain a nuclear magnetic resonance signal (the main imaging echo 507) by the main imaging (S303 in FIG. 3). Additionally, the main imaging sequence may not be executed at this timing, and the main imaging may be performed before this timing and store the obtained main imaging echo 507 in the storage media 111 to read out and use it from the storage media 111.

The inhomogeneous static magnetic field elimination unit 203 and the image reconstruction unit 204 generate a reconstruction image in which phase components by static magnetic field inhomogeneity was eliminated using the frequency band of phase components caused by static magnetic field inhomogeneity calculated in S302 and the main imaging echo 507 obtained in S303 (S304). As the elimination method, there is a method (a process in a k-space) where the image after inhomogeneous static magnetic field elimination 509 is reconstructed from the echo after inhomogeneous static magnetic field elimination 508 after a frequency band of phase components caused by static magnetic field inhomogeneity is eliminated from the main imaging echo 507 to obtain the echo 508.

Also, it is possible to use a method (a process in an image space) where the image after inhomogeneous static magnetic field elimination 509 is obtained by eliminating phase components caused by static magnetic field inhomogeneity from a reconstruction image after an image is reconstructed from the main imaging echo 507. In both cases, it is possible to use a method to eliminate the phase components of the above frequency band from the echo and the reconstruction image by applying a filter after generating the filter 506 to eliminate the phase components of the above frequency band. An example of the detailed process will be described in an embodiment later.

A reconstruction image where phase components caused by static magnetic field inhomogeneity were eliminated is to be displayed on the display device 110 by the image display unit 205 of the image processing unit 12 (S305 in FIG. 3).

As described above, according to the present embodiment, because a frequency range of phase components caused by static magnetic field inhomogeneity can be calculated by preliminary imaging, a frequency range of an inhomogeneous static magnetic field in an imaging space for main imaging can be calculated. Hence, because phase components caused by static magnetic field inhomogeneity can be eliminated by signal processing for a nuclear magnetic resonance process obtained in main imaging, low-frequency phase components caused by static magnetic field inhomogeneity can be separated from local high-frequency phase components in which important phase information for image diagnosis appears.

Also, by calculating a frequency band phase components caused by static magnetic field inhomogeneity in preliminary imaging, artifacts by static magnetic field inhomogeneity can be eliminated regardless of a static magnetic field intensity, an imaging sequence, an imaging parameter, factors such as a magnetization density inside an object and the relaxation time, and an influence of an imaging method in main imaging. Therefore, comparing to a case where filter processing by a fixed frequency band eliminates phase components caused by static magnetic field inhomogeneity, it is hard for a low-frequency phase to remain, and artifacts in an image can be reduced more.

First Embodiment

Hereinafter, specific examples of the frequency band calculation process (S302) by the frequency band calculation unit 202 in FIG. 2 described above and the generation process of the image after inhomogeneous static magnetic field elimination (S304) by the inhomogeneous static magnetic field elimination unit 203 as well as the image reconstruction unit 204 will be described using FIG. 6. In the present embodiment, phase components caused by static magnetic field inhomogeneity are eliminated in a k-space from a main imaging echo.

That is, the inhomogeneous static magnetic field elimination unit 203 generates a low-frequency phase image by performing inverse Fourier transform for low-frequency phase data equal to or less than a threshold frequency to generate a filter from the low-frequency phase image. By applying the filter to a nuclear magnetic resonance signal obtained in main imaging, phase components of a frequency band are eliminated. For example, the inhomogeneous static magnetic field elimination unit 203 uses data where Fourier transform was performed for an image in which a pixel value of a low-frequency phase image had been converted into an inverse number as a filter. By multiplying the filter by a nuclear magnetic resonance signal obtained in main imaging, phase components of a frequency band are eliminated.

[Step S601]

Figure 6:
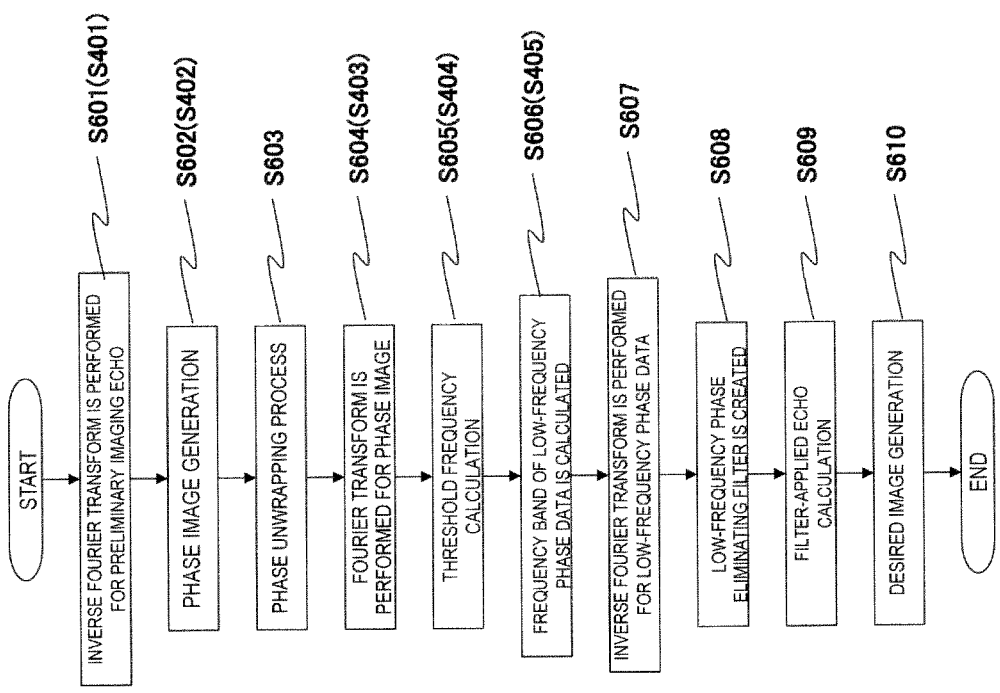
FIG. 6 is a flow chart showing a processing procedure of the first embodiment.

The phase image generation unit 21 of the frequency band calculation unit 202 performs inverse Fourier transform IFT(x) respectively for a real part Epr and an imaginary part Epi of the preliminary imaging echo 501 of a complex number obtained at S301 in FIG. 3 to calculate the real-part image (Spr) 502 and the imaginary-part image (Spi) 503 (the formula (1) and formula (2)) (S601 in FIG. 6 (equivalent to S401)).

[Number 1]

$$Spr = \text{IFT}(Epr) \quad \text{Formula (1)}$$

[Number 2]

$$Spi = \text{IFT}(Epi) \quad \text{Formula (2)}$$

[Step S602]

Regarding pixel values of the real-part image (Spr) 502 and the imaginary-part image (Spi) 503 as a complex value for each pixel, a phase value $Sp_p$ at the pixel is calculated by the following formula (3) to generate the phase image ($Sp_p$) 504 whose pixel value is the phase value $Sp_p$ (S602 (equivalent to S402)).

[Number 3]

$$Sp_p = \arctan\left(\frac{Spi}{Spr}\right) \quad \text{Formula (3)}$$

[Step S603]

In this step, a phase unwrapping process may be performed for the calculated phase image ($Sp_p$) 504 (S603). The phase unwrapping process, for example, in a case where a phase value of a pixel (x, y) is π; a phase value of the adjacent pixel (x+1, y) is –π, that is, corrects a phase value of a pixel subsequent to a pixel (x+1, y) in a case where the phase value of the adjacent pixel has a steep change so that it has an entirely gradual change (a series of phase values). Detailed processing contents of the phase unwrapping process includes various known processing methods such as a method of converting into the (0, 2π) range and a method of converting into the (–π, π) range, but the process contents are not limited to these methods. When the phase unwrapping process is expressed as Unwrap (A) like a function, a phase image $Sp_{pu}$ converted into the (–π, π) range after phase unwrapping is to be expressed as the formula (4) using a phase image $Sp_p$ before the phase unwrapping process.

[Number 4]

$$Sp_{pu} = \text{Unwrap}(Sp_p) \quad \text{Formula (4)}$$

[Step S604]

Next, the threshold frequency calculation unit 22 handles data where pixel values of a phase image $Sp_{pu}$ after the phase unwrapping process are aligned as periodical data in a finite length of a single line and performs Fourier transform FT(x) (S604 (equivalent to S403)). The Fourier-transformed data becomes phase data $Dp_p$ (the formula (5)).

[Number 5]

$$Dp_p = \text{FT}(SP_{pu}) \quad \text{Formula (5)}$$

[Step S605]

Figure 7:
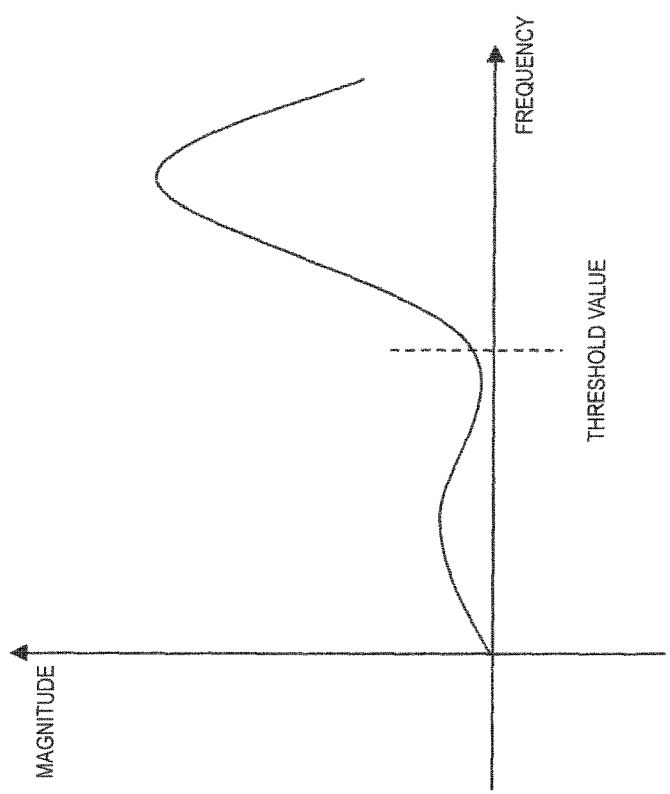
FIG. 7 is a graph showing a frequency distribution histogram and a threshold frequency of phase data in the first embodiment.

From frequency distribution of the phase data $Dp_p$, how much of what frequency component is included can be known. Since a frequency component of phase data caused by static magnetic field inhomogeneity is a low frequency, the threshold frequency calculation unit 22 calculates a threshold frequency to separate low-frequency phase data from high-frequency phase data (S605 (equivalent to S404)). For example, as shown in FIG. 7, a method where a frequency distribution histogram of phase data $Dp_p$ is calculated; the center of the histogram is calculated using a weighted average method and an addition-averaging method; and the center is specified as a threshold frequency can be used. Also, the separation can be performed using a discriminant analysis method, p-tile method, etc. Specifically, in a case where the separation is performed using the discriminant analysis method, a threshold frequency to separate a low frequency phase from a high frequency is calculated according to the following procedure.

(1) A power spectrum of phase data $Dp_p$ is calculated to create a histogram where the horizontal axis a frequency; the vertical axis is a degree as shown in FIG. 7.

(2) A discriminant analysis method is applied to the histogram to calculate a threshold frequency shown with a broken line in FIG. 7.

[Step S606]

The threshold frequency calculation unit 22 calculates a band of frequency phase data equal to or less than a phase threshold (low-frequency phase data $Dp_l$) calculated from phase data $Dp_p$ to separate from frequency phase data larger than a phase threshold (high-frequency phase data $Dp_h$) (S606 (equivalent to S405)). The low-frequency phase data $Dp_l$ is a frequency band of phase data caused by static magnetic field inhomogeneity. The frequency phase data larger than a phase threshold (high-frequency phase data $Dp_h$) is phase data caused by a condition other than static magnetic field inhomogeneity.

[Step S607]

Next, the inhomogeneous static magnetic field elimination unit 203 creates a filter to eliminate the phase components of the frequency band calculated from the main imaging echo 507 in S405. In order to create the filter, in the present first embodiment, the inhomogeneous static magnetic field elimination unit 203 performs inverse Fourier transform for the low-frequency phase data Dpi calculated in S606 to calculate a low-frequency phase image Sp (the formula (6)).

[Number 6]

$$Sp_l = \text{IFT}(Dp_l) \quad \text{Formula (6)}$$

[Step S608]

Using the calculated low-frequency phase image $Sp_l$, the inhomogeneous static magnetic field elimination unit 203 creates a low-frequency phase elimination filter $Fp_l$. The present embodiment, as the easiest method, performs Fourier transform for data in which inverse numbers of the respective pixel values of the low-frequency phase image Sp are arranged to create the low-frequency phase elimination filter $Fp_l$ (the formula (7)).

[Number 7]

$$Fp_i = FT\left(\frac{1}{Sp_i}\right) \quad \text{Formula (7)}$$

[Step S609]

The inhomogeneous static magnetic field elimination unit 203 multiplies a real part Emr and a an imaginary part Emi of the main imaging echo 507 respectively by the low-frequency phase elimination filter $Fp_l$ to calculate a real part Fmr and a an imaginary part Fmi of a filtered echo (the echo after inhomogeneous static magnetic field elimination 508) (the formulas (8) and (9)).

[Number 8]

$$Fmr = Emr \times Fp_l \quad \text{Formula (8)}$$

[Number 9]

$$Fmi = Emi \times Fp_l \quad \text{Formula (9)}$$

[Step S610]

Inverse Fourier transform is respectively performed for a real part Fmr and a an imaginary part Fmi of the echo after inhomogeneous static magnetic field elimination 508 to calculate a real-part image Smr and an imaginary-part image Smi (the formulas (10) and (11)).

In order to generate a magnitude image $Sm_m$, finally, the formula (12) is used to generate the magnitude image from pixel values of a real-part image Smr and an imaginary-part image Smi. Also, by calculating arctan (Smr/Smi), a phase image can be absolutely generated.

[Number 10]

$$Smr = \text{IFT}(Fmr) \quad \text{Formula (10)}$$

[Number 11]

$$Smi = \text{IFT}(Fmi) \quad \text{Formula (11)}$$

[Number 12]

$$Sm_m = \sqrt{Smi^2 + Smr^2} \quad \text{Formula (12)}$$

As described above, by applying the present embodiment, because only low-frequency phase components caused by static magnetic field inhomogeneity can be eliminated from the main imaging echo 507, an image in which artifacts by a global phase caused by static magnetic field inhomogeneity were reduced can be obtained for a final display image.

Figure 8:
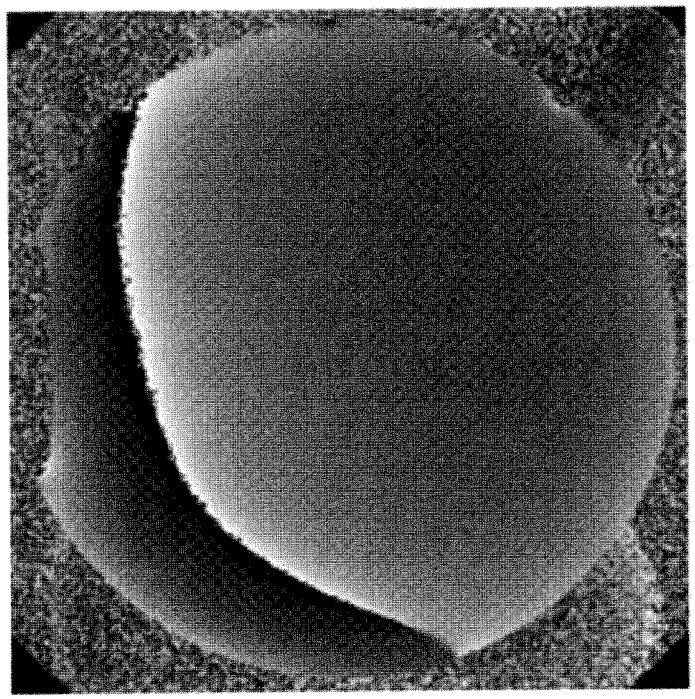
FIG. 8 is an example of a phase image obtained without applying the present invention.
Figure 9:
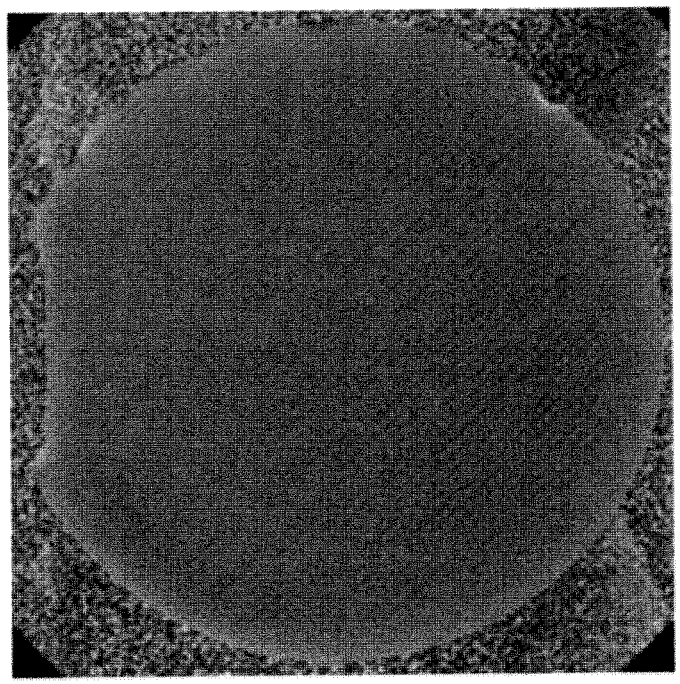
FIG. 9 is an example of a phase image obtained by the first embodiment.

As an example, FIG. 8 shows a phase image generated without applying the present embodiment that had been generated from the main imaging echo 507, and FIG. 9 shows a phase image generated by applying the process of FIG. 6 in the first embodiment. Compared to FIG. 8, the phase image of FIG. 9 to which the present embodiment was applied is an image that has no phase discontinuity and no global artifacts caused by static magnetic field inhomogeneity also.

Second Embodiment

Although phase components in a frequency band caused by static magnetic field inhomogeneity in a k-space were eliminated by applying a filter to the main imaging echo 507 in the above first embodiment, an image in which phase components caused by static magnetic field inhomogeneity are eliminated in an image space by applying a filter to a reconstruction image of the main imaging echo 507 is obtained in the second embodiment. The process will be described using FIG. 10.

That is, the inhomogeneous static magnetic field elimination unit 203 performs inverse Fourier transform for the low-frequency phase data equal to or less than a threshold frequency to generate a low-frequency phase image, generates a filter from the low-frequency phase image, and applies the filter to an image generated from a nuclear magnetic resonance signal obtained in main imaging to eliminate phase components in a frequency band. For example, the inhomogeneous static magnetic field elimination unit 203, regarding a low-frequency phase image as a filter, eliminates phase components in a frequency band by dividing a pixel value of an image generated from a nuclear magnetic resonance signal obtained in main imaging by a pixel value of the low-frequency phase image.

[Steps S601 to S607]

The respective steps from S601 to S606 are similar to the first embodiment, and the descriptions are omitted. In S607, similarly to the first embodiment, inverse Fourier transform is performed for a low-frequency phase data $Dp_l$ calculated in S606 to calculate a low-frequency phase image $Sp_l$ (the formula (6)).

[Step S608']

Next, using a pixel value (phase value) of the low-frequency phase image $Sp_l$, a complex number Cp whose argument is a phase value Sp and the size is 1 is generated to generate respectively a low-frequency real-part image Cpr whose real-part component is specified as a pixel value and a low-frequency imaginary-part image Cpi whose imaginary-part component is specified as a pixel value. These low-frequency real-part image Cpr and low-frequency imaginary-part image Cpi are used as a filter in the second embodiment to eliminate phase components caused by static magnetic field inhomogeneity.

[Step S609']

Next, the filter generated in Step S608' is applied to an image reconstructed from the main imaging echo 507 to generate an image in which phase components in a frequency band caused by static magnetic field inhomogeneity were eliminated.

First, inverse Fourier transform is performed for a real part Emr and an imaginary part Emi of the main imaging echo 507 to calculate an after-FT real-part image Smr and an after-FT imaginary-part image Smi (the formulas (13) and (14)).

[Number 13]

$$Smr = IFT(Emr) \quad \text{Formula (13)}$$

[Number 14]

$$Smi = IFT(Emi) \quad \text{Formula (14)}$$

The respective pixel values of the calculated after-FT real-part image Smr and the after-FT imaginary-part image Smi are divided by the respective pixel values of a low-frequency real-part image Cpr and a low-frequency imaginary-part image Cpi that are filters with the formulas (15) and (16) to generate respectively a filtered real-part image Fmr and a filtered imaginary-part image Fmi whose pixel values are the obtained values Fmr and Fmi.

[Number 15]

$$Fmr = \frac{Smr \times Cpr + Smi \times Cpi}{\sqrt{Cpr^2 + Cpi^2}} \quad \text{Formula (15)}$$

[Number 16]

$$Fmr = \frac{Smi \times Cpr - Smr \times Cpi}{\sqrt{Cpr^2 + Cpi^2}} \quad \text{Formula (16)}$$

[Step S610']

In order to generate a magnitude image $Sm_m$ finally, a pixel value of the magnitude image $Sm_m$ is calculated by the formula (17) from pixel values of the filtered real-part image Fmr and the filtered imaginary-part image Fmi. Also, by calculating arctan (Smr/Smi), a phase image can be absolutely generated.

[Number 17]

$$Sm_m = \sqrt{Fmi^2 + Fmr^2} \quad \text{Formula (17)}$$

Third Embodiment

Figure 11:
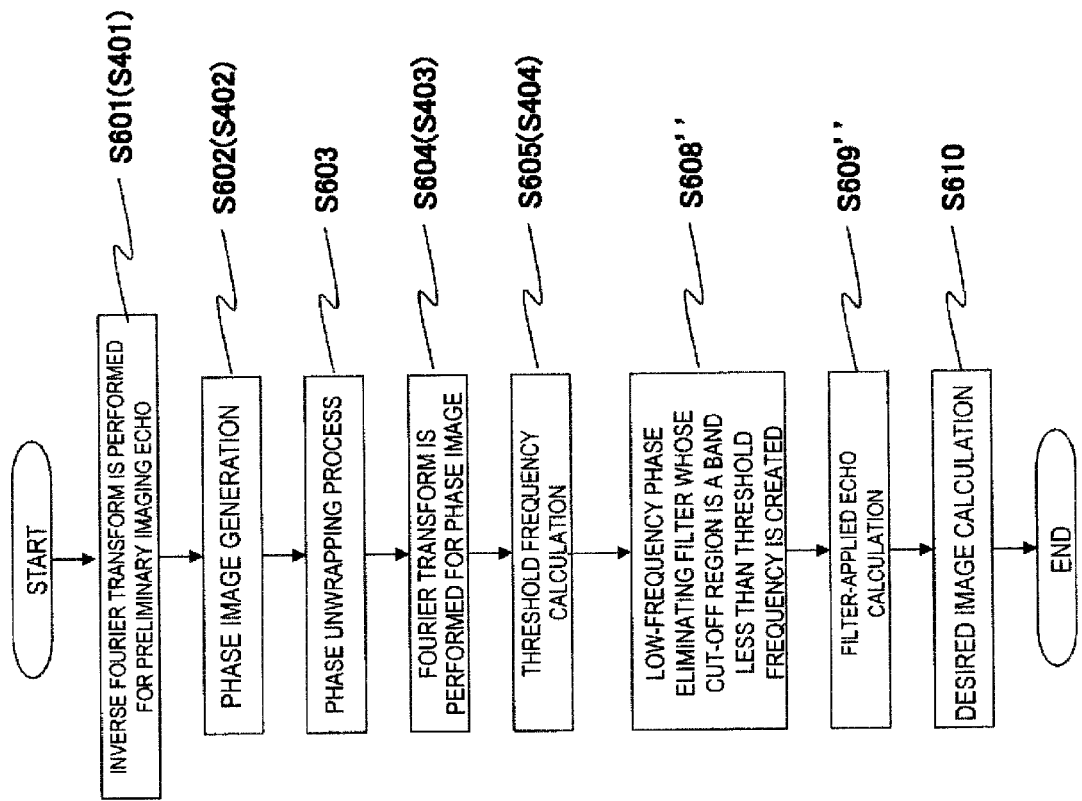
FIG. 11 is a flow chart showing a processing procedure of the third embodiment.

As the third embodiment, description will be made using FIG. 11 for a process of eliminating phase components in a frequency band caused by static magnetic field inhomogeneity from the main imaging echo 507 using a low-frequency phase eliminating filter after creating the filter from a threshold frequency calculated Step S605 in the first embodiment.

That is, in the third embodiment, the inhomogeneous static magnetic field elimination unit 203 generates a high-frequency pass filter passing a frequency band larger than a threshold value and applies it to a nuclear magnetic resonance signal obtained in main imaging to eliminate phase components in a frequency band caused by static magnetic field inhomogeneity. For example, the inhomogeneous static magnetic field elimination unit 203 filters the nuclear magnetic resonance signal obtained in main imaging with a low-frequency phase eliminating filter where Fourier transform was performed for the high-frequency pass filter to eliminate phase components of the above frequency band.

[Steps S601 to S605]

The respective steps from S601 to S605 are similar to the first embodiment, and a threshold frequency will be calculated in Step S605. Additionally, the third embodiment does not perform calculation of a frequency band and inverse Fourier transform of low-frequency phase data in Steps S607 and S607 of the first embodiment.

[Step S608']

Figure 12:
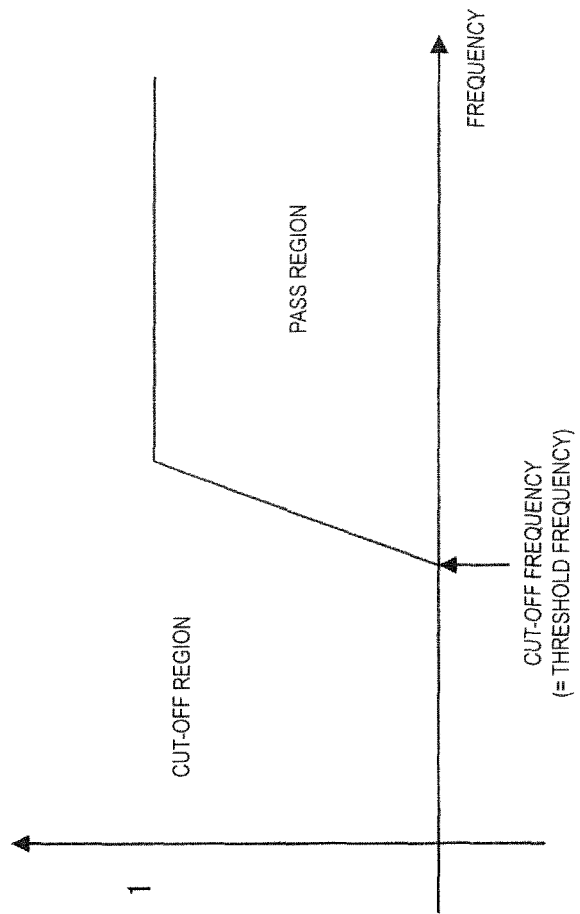
FIG. 12 is a graph showing a high-frequency region pass filter of the third embodiment.

Next, a high-frequency region pass filter $DF_{hp}$ is created as shown in FIG. 12. The high-frequency region pass filter $DF_{hp}$ is that whose cut-off frequency is a threshold frequency "threshold" and is created so that a low-frequency band lower than a threshold frequency is specified as a cut-off region with a high-frequency band equal to or more than the threshold frequency specified as a pass region. At this point, in the graph of FIG. 12, the vertical axis is a coefficient, and the horizontal axis is a frequency. A low-frequency phase eliminating filter $SF_{hp}$ is created by performing Fourier transform for the high-frequency region pass filter $DF_{hp}$ (the formula (18)).

[Number 18]

$$SF_{hp} = FT(DF_{hp}) \quad \text{Formula (18)}$$

[Step S609"]

A low-frequency phase eliminating filter $SF_{hp}$ is multiplied by a real part Emr and an imaginary part Emi of the main imaging echo 507 respectively to calculate a real part Fmr and an imaginary part Fmi of a filtered echo (the echo after inhomogeneous static magnetic field elimination 508) (the formulas (19) and (20)).

[Number 19]

$$Fmr = Emr \times SF_{hp} \quad \text{Formula (19)}$$

[Number 20]

$$Fmi = Emi \times SF_{hp} \quad \text{Formula (20)}$$

[Step S610]

From the real part Fmr and the imaginary part Fmi of the echo after inhomogeneous static magnetic field elimination 508, similarly to Step S610 of the first embodiment, the formulas (10), (11), (12), etc. are used to generate a desired magnitude image $Sm_m$ and a phase image.

Fourth Embodiment

Figure 13:
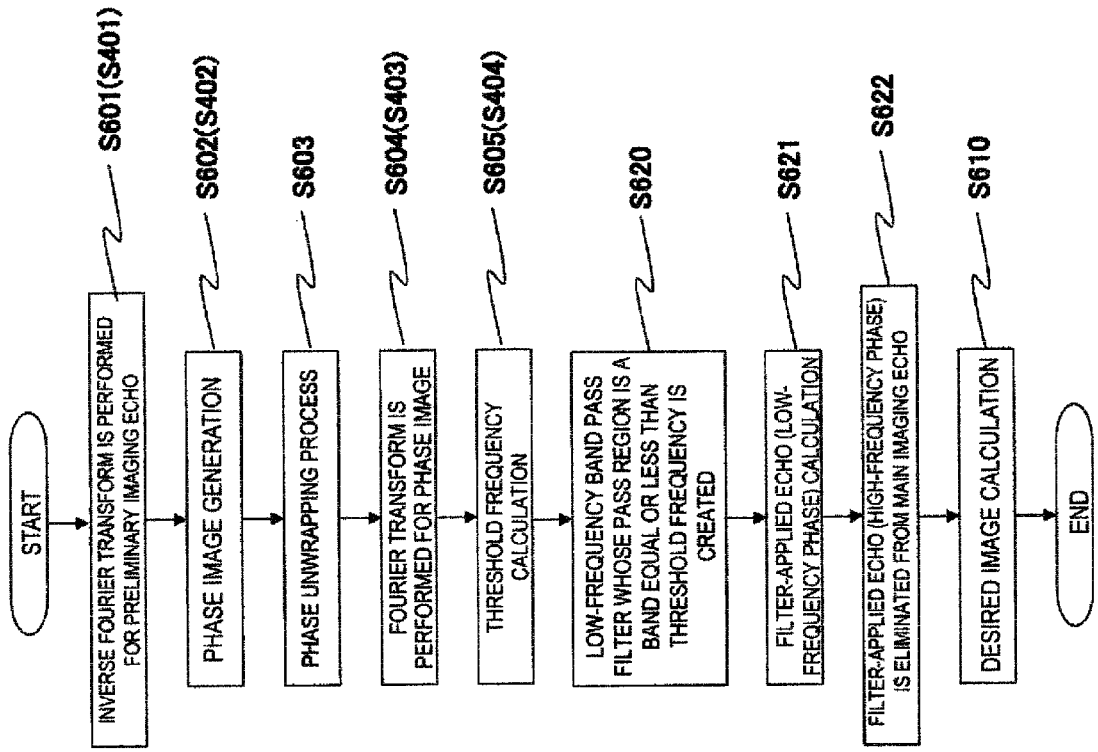
FIG. 13 is a flow chart showing a processing procedure of the fourth embodiment.

In the fourth embodiment, phase components (low-frequency phase components) in a frequency band caused by static magnetic field inhomogeneity are eliminated while signal intensity reduction of high-frequency phase components of the main imaging echo 507 is being prevented. First, a high-frequency phase eliminating filter is applied to the main imaging echo 507, phase components of a higher frequency than a threshold frequency are eliminated, and an echo in which only low-frequency phase components remain is used to eliminate only the low-frequency phase components from the main imaging echo 507. Hence, because the filter is not applied to high-frequency phase components of the main imaging echo 507, the high-frequency phase components can be obtained without signal intensity reduction. This processing step will be described using FIG. 13.

Specifically, the inhomogeneous static magnetic field elimination unit 203 generates a low-frequency pass filter passing a frequency band smaller than a threshold frequency, applies the filter to a nuclear magnetic resonance signal obtained in main imaging to a nuclear magnetic resonance signal in the frequency band, and subtracts it from the nuclear magnetic resonance signal obtained in main imaging to obtain a signal where phase components in a frequency band caused by static magnetic field inhomogeneity are eliminated. For example, the inhomogeneous static magnetic field elimination unit 203 multiplies a high-frequency phase eliminating filter in which Fourier transform was performed for a low-frequency pass filter by the nuclear magnetic resonance signal obtained in main imaging to obtain a nuclear magnetic resonance signal in the above frequency band.

[Steps S601 to S605]

The respective steps from S601 to S605 are similar to the first embodiment, and a threshold frequency will be calculated in Step 605. Additionally, the fourth embodiment does not perform calculation of a frequency band and inverse Fourier transform of low-frequency phase data in Steps 606 and 607 of the first embodiment.

[Step S620]

Next, as shown in FIG. 14, a low-frequency region pass filter $DF_{lp}$ is created, whose cut-off frequency is a threshold frequency "threshold" and where a frequency larger than a threshold frequency is specified as a cut-off region with a pass region being equal to or less than the threshold frequency. Fourier transform is performed for the low-frequency region pass filter $DF_{lp}$ to create a high-frequency phase eliminating filter $SF_{lp}$ (the formula (21)).

[Number 21]

$$SF_{lp}=FT(DF_{lp}) \quad \text{Formula (21)}$$

[Step S621]

The high-frequency phase eliminating filter $SF_{lp}$ is applied to a real part Emr and an imaginary part Emi of main imaging echoes to calculate filtered echoes $Fmr_{lp}$ and $Fmi_{lp}$ (the formulas (22) and (23)).

[Number 22]

$$Fmr_{lp}=Emr \times SF_{lp} \quad \text{Formula (22)}$$

[Number 23]

$$Fmi_{lp}=Emi \times SF_{lp} \quad \text{Formula (23)}$$

[Step S622]

The high-frequency phase elimination filtered echoes $Fmr_{lp}$ and $Fmi_{lp}$ calculated in S621 are those in which only low-frequency components equal to or less than a phase threshold "threshold" remain. That is, a real part Emr and an imaginary part Emi of main imaging echoes are divided by a real part $Fmr_{lp}$ and an imaginary part $Fmi_{lp}$ of the high-frequency phase elimination filtered echoes, which can calculate a real part Fmr and an imaginary part Fmi of the echo after inhomogeneous static magnetic field elimination 508 (the formulas (24) and (25)).

[Number 24]

$$Fmr = \frac{Fmr \times Fmr_{lp} + Fmi \times Fmi_{lp}}{\sqrt{Fmr_{lp}^2 + Fmi_{lp}^2}} \quad \text{Formula (24)}$$

[Number 25]

$$Fmr = \frac{Fmi \times Fmr_{lp} - Fmr \times Fmi_{lp}}{\sqrt{Fmr_{lp}^2 + Fmi_{lp}^2}} \quad \text{Formula (25)}$$

[Step S610]

From the real part Fmr and the imaginary part Fmi of the echo after inhomogeneous static magnetic field elimination 508, similarly to Step 610 of the first embodiment, the formulas (10), (11), (12), etc. are used to generate a desired magnitude image $Sm_m$ and a phase image.

In the present fourth embodiment, because high-frequency phase components that are low-frequency phase elimination filtered echoes (the echo after inhomogeneous static magnetic field elimination 508) are components to which a filter are not applied, the signal intensity is large. Therefore, a clear image whose contrast ratio is large can be obtained as a magnitude image $Sm_m$ and a phase image to be generated in S610.

DESCRIPTION OF REFERENCE NUMERALS

10: imaging unit, 11: control unit, 12: image processing unit, 21: phase image generation unit, 22: threshold frequency calculation unit, 101: magnet, 102: gradient magnetic field coil, 103: object, 104: sequencer, 105: gradient magnetic field power source, 106: high-frequency generation device, 107: probe, 108: receiver, 109: calculator, 110: display device, 111: storage media, 201: echo measurement unit, 202: frequency band calculation unit, 203: inhomogeneous static magnetic field elimination unit, 204: image reconstruction unit, 205: image display unit

The invention claimed is:

1. A magnetic resonance imaging apparatus comprising:
an imaging unit detecting a nuclear magnetic resonance signal generated from an object after applying a high-frequency magnetic field and a gradient magnetic field to the object placed in a static magnetic field;
a control unit controlling operation of the imaging unit; and
an image processing unit performing calculation for the nuclear magnetic resonance signal and generating an image,
wherein the control unit allows the imaging unit to execute predetermined preliminary imaging and main imaging, and
the image processing unit includes:
a frequency band calculation unit calculating a frequency band of phase components caused by inhomogeneity of the static magnetic field from the nuclear magnetic resonance signal obtained by the preliminary imaging; and
an inhomogeneous static magnetic field elimination unit eliminating phase components in the frequency band from either of the nuclear magnetic resonance signal obtained by the main imaging or an image reconstructed from the nuclear magnetic resonance signal obtained by the main imaging.

2. The magnetic resonance imaging apparatus according to claim 1,
wherein the preliminary imaging is to obtain two sets of nuclear magnetic resonance signals to image a predetermined site with the echo time shifted, and
the frequency band calculation unit includes a phase image generation unit generating a phase image that shows distribution of phase differences of the two sets of nuclear magnetic resonance signals obtained in the predetermined site from the two sets of nuclear magnetic resonance signals obtained by the predetermined preliminary imaging and a threshold frequency calculation unit calculating the frequency distribution of phase data obtained by performing Fourier transform for the phase image, calculating a threshold frequency to separate the phase data into high-frequency phase data and low-frequency phase data based on the frequency distribution, and specifying a range equal to or less than the threshold frequency as the frequency band.

3. The magnetic resonance imaging apparatus according to claim 2,
wherein the threshold frequency calculation unit uses at least one process of a discriminant analysis method, weighted average method, addition-averaging method, and p-tile method for frequency distribution of the phase differences to calculate the threshold frequency.

4. The magnetic resonance imaging apparatus according to claim 1,
wherein the inhomogeneous static magnetic field elimination unit generates a filter eliminating phase components in the frequency band and applies the filter to a nuclear magnetic resonance signal obtained in the main imaging or an image generated from the nuclear magnetic resonance signal obtained in the main imaging to eliminate the phase components in the frequency band.

5. The magnetic resonance imaging apparatus according to claim 2,
wherein the inhomogeneous static magnetic field elimination unit generates a low-frequency phase image by performing inverse Fourier transform for the low-frequency phase data equal to or less than the threshold frequency, generates a filter from the low-frequency phase image, and applies the filter to a nuclear magnetic resonance signal obtained in the main imaging or an image generated from the nuclear magnetic resonance signal obtained in the main imaging to eliminate the phase components in the frequency band.

6. The magnetic resonance imaging apparatus according to claim 5,
wherein the inhomogeneous static magnetic field elimination unit uses data in which Fourier transform was performed for the low-frequency phase image whose pixel value had been changed to an inverse number as the filter and multiplies the filter by a nuclear magnetic resonance signal obtained in the main imaging to eliminate the phase components in the frequency band.

7. The magnetic resonance imaging apparatus according to claim 5,
wherein the inhomogeneous static magnetic field elimination unit specifies the low-frequency phase image as the filter and divides a pixel value of an image generated from a nuclear magnetic resonance signal obtained in the main imaging by a pixel value of the low-frequency phase image to eliminate the phase components in the frequency band.

8. The magnetic resonance imaging apparatus according to claim 2,
wherein the inhomogeneous static magnetic field elimination unit generates a high-frequency pass filter passing a frequency band larger than the threshold frequency and applies it to a nuclear magnetic resonance signal obtained in the main imaging to eliminate the phase components in the frequency band.

9. The magnetic resonance imaging apparatus according to claim 8,
wherein the inhomogeneous static magnetic field elimination unit multiplies a low-frequency phase elimination filter where Fourier transform was performed for the high-frequency pass filter by a nuclear magnetic resonance signal obtained in the main imaging to eliminate the phase components in the frequency band.

10. The magnetic resonance imaging apparatus according to claim 2,
wherein the inhomogeneous static magnetic field elimination unit generates a low-frequency pass filter passing a frequency band smaller than the threshold frequency, applies it to a nuclear magnetic resonance signal obtained in the main imaging to obtain a nuclear magnetic resonance signal of the frequency band, and eliminates it from the nuclear magnetic resonance signal obtained in the main imaging to obtain a signal in which phase components in the frequency band was eliminated.

11. The magnetic resonance imaging apparatus according to claim 10,
wherein the inhomogeneous static magnetic field elimination unit multiplies a high-frequency phase elimination filter where Fourier transform was performed for the low-frequency pass filter by a nuclear magnetic resonance signal obtained in the main imaging to obtain a nuclear magnetic resonance signal in the frequency band.

12. A magnetic resonance imaging method,
wherein phase components in a frequency band caused by inhomogeneity of the static magnetic field are calculated from a nuclear magnetic resonance signal obtained by performing predetermined preliminary imaging for an object placed in a static magnetic field, and
phase components in the frequency band are eliminated from an image generated from a nuclear magnetic resonance signal obtained by performing predetermined main imaging for the object placed in the static magnetic field.

* * * * *